United States Patent
Narimatsu et al.

(10) Patent No.: US 6,869,403 B2
(45) Date of Patent: Mar. 22, 2005

(54) BLOOD-PRESSURE DETERMINING APPARATUS

(75) Inventors: Kiyoyuki Narimatsu, Komaki (JP); Akira Tampo, Komaki (JP); Toshihiko Ogura, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

(21) Appl. No.: 10/370,691

(22) Filed: Feb. 24, 2003

(65) Prior Publication Data

US 2003/0236465 A1 Dec. 25, 2003

(30) Foreign Application Priority Data

Jun. 20, 2002 (JP) ...................................... 2002-180368

(51) Int. Cl.⁷ ................................................ A61B 5/00
(52) U.S. Cl. ..................................... 600/500; 600/490
(58) Field of Search ......................... 600/490, 493–496, 600/500, 485

(56) References Cited

U.S. PATENT DOCUMENTS

| | | | |
|---|---|---|---|
| 4,699,152 A | | 10/1987 | Link |
| 5,261,414 A | * | 11/1993 | Aung et al. ................. 600/496 |
| 5,590,661 A | * | 1/1997 | Ohmori et al. ............. 600/485 |
| 5,772,601 A | * | 6/1998 | Oka et al. ................... 600/495 |
| 5,980,464 A | * | 11/1999 | Tsuda .......................... 600/485 |
| 6,520,919 B1 | * | 2/2003 | Nunome et al. ............ 600/494 |
| 2001/0037068 A1 | | 11/2001 | Goto et al. |
| 2003/0097074 A1 | * | 5/2003 | Oka et al. ................... 600/490 |

FOREIGN PATENT DOCUMENTS

| EP | 0 655 219 A1 | 5/1995 |
|---|---|---|
| JP | 4-58973 | 9/1992 |
| JP | 5-3858 A | 1/1993 |

* cited by examiner

*Primary Examiner*—Robert L. Nasser
(74) *Attorney, Agent, or Firm*—Oliff & Berridge, PLC

(57) ABSTRACT

A blood-pressure estimating apparatus, including a pulse-wave detecting device which detects a pulse wave from a portion of a living subject, a blood-pressure measuring device which includes an inflatable cuff adapted to be worn on the portion of the subject and measures, with the cuff, a diastolic blood pressure and a systolic blood pressure of the portion of the subject, and a mean-blood-pressure estimating device which converts, based on a minimum magnitude and a maximum magnitude of the pulse wave detected by the pulse-wave detecting device and the diastolic and systolic blood pressure measured by the blood-pressure measuring device, a magnitude of a gravity center of an area defined by the pulse wave into an estimated mean blood pressure of the portion of the subject.

8 Claims, 11 Drawing Sheets

BLOOD-PRESSURE DETERMINING APPARATUS

BACKGROUND OF THE INVENTION

1. Field of the Invention

The present invention relates to a blood-pressure determining apparatus which determines a blood pressure of a portion of a living subject; such as a brachial portion or a cervical portion of the subject.

2. Related Art Statement

When a disease of a central artery of a living subject, such as coronary artery or aorta ascendens, is inspected, it is desirable to measure a blood pressure of a central portion of the subject. However, it is not easy to measure a blood pressure of a more central portion than a brachial portion. For example, it is difficult to accurately measure a blood pressure of a cervical portion, i.e., a carotid-artery blood pressure, even in an invasive method. Thus, it has been practiced to measure a blood pressure of a brachial portion also when a disease of a central artery such as coronary artery or aorta ascendens, is inspected.

Meanwhile, it is known that when blood pressure values of a living subject who is taking a face-up position are measured, diastolic and mean blood pressure of a carotid artery of the subject (hereinafter, referred to as cervical diastolic and mean blood pressure CBP(DIA), CBP(MEAN), respectively) are substantially equal to diastolic and mean blood pressure of a brachial portion of the subject (hereinafter, referred to as brachial diastolic and mean blood pressure BBP(DIA), BBP(MEAN), respectively), respectively, but a systolic blood pressure of the carotid artery (hereinafter, referred to as cervical systolic blood pressure CBP(SYS)) is not equal to a systolic blood pressure of the brachial portion (hereinafter, referred to as brachial systolic blood pressure BBP(SYS)).

A carotid-pulse-wave detecting device has recently been improved and can accurately detect a waveform of a carotid pulse wave, wc. However, an absolute blood pressure in a carotid artery cannot be accurately determined based on only the carotid pulse wave wc detected by the carotid-pulse-wave detecting device. Hence, it is considered to convert, based on a brachial blood pressure BBP measured using a cuff, a carotid pulse wave wc detected by the carotid-pulse-wave detecting device, into a cervical blood pressure CBP.

FIG. 1 shows a heartbeat-synchronous pulse of a carotid pulse wave wc detected by the carotid-pulse-wave detecting device. Since a minimum-magnitude, a, an area-gravity-center magnitude, b, and a maximum magnitude, c, of the heartbeat-synchronous pulse of the carotid pulse wave wc correspond to a cervical diastolic blood pressure CBP(DIA), a cervical mean blood pressure CBP(MEAN), and a cervical systolic blood pressure CBP(SYS), respectively, a relationship represented by the following Expression 1 is obtained:

$$c-a:b-a=CBP(SYS)-CBP(DIA):CBP(MEAN)-CBP(DIA) \quad \text{(Expression 1)}$$

As described above, cervical diastolic and mean blood pressure CBP(DIA), CBP(MEAN) are substantially equal to brachial diastolic and mean blood pressure BBP(DIA), BBP(MEAN), respectively. Therefore, a cervical systolic blood pressure CBP(SYS) can be determined by replacing, in Expression 1, the cervical diastolic and mean blood pressure CBP(DIA), CBP(MEAN) with the brachial diastolic and mean blood pressure BBP(DIA), BBP(MEAN), respectively.

However, in each blood-pressure measuring operation using a cuff, an accurate brachial diastolic blood pressure BBP(DIA) is measured, but an accurate brachial mean blood pressure BBP(MEAN) may not be measured. Therefore, if a brachial mean blood pressure BBP(MEAN) measured using a cuff is used in place of a cervical mean blood pressure CBP(MEAN), the thus obtained cervical mean blood pressure CBP(MEAN) and a cervical systolic blood pressure CBP(SYS) calculated based on the cervical mean blood pressure CBP(MEAN) may not be sufficiently accurate.

SUMMARY OF THE INVENTION

The present invention has been developed in the above-described background. An initial object of the Inventors was to provide a brachial-blood-pressure estimating apparatus capable of accurately estimating a brachial mean blood pressure of a living subject, and a cervical-blood-pressure estimating apparatus including the brachial-blood-pressure estimating apparatus and capable of accurately estimating a cervical blood pressure of a living subject. To achieve the object, the Inventors have carried out extensive studies and found the following facts: A brachial pulse wave, wb, detected from a brachial portion of a living subject is highly accurate, and brachial diastolic and systolic blood pressure BBP(DIA), BBP(SYS) measured using a cuff are highly reliable. Therefore, if a brachial mean blood pressure BBP(MEAN) is estimated, like the above-described cervical systolic blood pressure CBP(SYS), based on a minimum magnitude, d, an area-gravity-center magnitude, e, and a maximum magnitude, f, of the brachial pulse wave wb and the brachial diastolic and systolic blood pressure BBP(DIA), BBP(SYS), the thus estimated brachial mean blood pressure BBP(MEAN) enjoys a high accuracy; and if the brachial mean blood pressure BBP(MEAN) is used, accurate cervical mean and systolic blood pressure CBP(MEAN), CBP(SYS) are estimated.

Moreover, the Inventors have found that the above-described technique to estimate brachial mean blood pressure can apply to the estimation of brachial diastolic blood pressure, that the same technique can apply to the estimation of mean or diastolic blood pressure of any other portion than brachial portion so long as a pulse wave can be detected and a blood pressure can be measured using a cuff, and that the technique to estimate cervical blood pressure based on brachial blood pressure can apply to the estimation of blood pressure of any other portion than cervical portion.

It is therefore a first object of the present invention to provide a first blood-pressure estimating apparatus which can accurately estimate a mean blood pressure of a first portion of a living subject; it is a second object of the present invention to provide a second blood-pressure estimating apparatus which can accurately estimate a diastolic blood pressure of a first portion of a living subject; and it is a third object of the present invention to provide a third blood-pressure estimating apparatus which includes the first or second blood-pressure estimating apparatus and can accurately estimate a blood pressure of a second portion of the subject that differs from the first portion.

The above object has been achieved by the present invention. According to a first aspect of the present invention, there is provided a blood-pressure estimating apparatus, comprising a first-pulse-wave detecting device which detects a first pulse wave from a first portion of a living subject; a blood-pressure measuring device which includes an inflatable cuff adapted to be worn on the first portion of the subject and measures, with the cuff, a diastolic blood pressure and a systolic blood pressure of the first portion of the subject; and a mean-blood-pressure estimating means for converting, based on a minimum magnitude and a maximum magnitude of the first pulse wave detected by the first-pulse-wave detecting device and the diastolic blood pressure and the systolic blood pressure measured by the blood-pressure measuring device, a magnitude of a gravity center of an area defined by the first pulse wave into an estimated mean blood pressure of the first portion of the subject.

According to this aspect, the first-pulse-wave detecting device detects an accurate first pulse wave from the first portion, the blood-pressure measuring device measures accurate diastolic and systolic blood pressure of the first portion, and the mean-blood-pressure estimating means estimates, based on a minimum magnitude, an area-gravity-center magnitude, and a maximum magnitude of the accurate first pulse wave and the accurate diastolic and systolic blood pressure, a mean blood pressure of the first portion. Therefore, the thus estimated mean blood pressure enjoys a high accuracy, and is useful in making a diagnosis. In addition, as described later, the accurate mean blood pressure of the first portion can be used to estimate an accurate blood pressure of a second portion different from the first portion.

The blood-pressure estimating apparatus in accordance with the first aspect of the present invention is useful in the case where the accuracy of measurement of mean blood pressure is lower than that of diastolic blood pressure. In fact, at present, the accuracy of mean blood pressure measured using a cuff is lower than that of diastolic blood pressure measured using the cuff. However, in future, the current blood-pressure determining algorithm may be so improved that the accuracy of measurement of mean blood pressure is increased and even exceeds that of diastolic blood pressure. The technical concept in accordance with the first aspect can also apply to the latter case in which the increased accuracy of mean blood pressure may exceed the accuracy of diastolic blood pressure, so as to estimate an accurate diastolic blood pressure.

According to a second aspect of the present invention, there is provided a blood-pressure estimating apparatus, comprising a first-pulse-wave detecting device which detects a first pulse wave from a first portion of a living subject; a blood-pressure measuring device which includes an inflatable cuff adapted to be worn on the first portion of the subject and measures, with the cuff, a mean blood pressure and a systolic blood pressure of the first portion of the subject; and a diastolic-blood-pressure estimating means for converting, based on an area-gravity-center magnitude and a maximum magnitude of the first pulse wave detected by the first-pulse-wave detecting device and the mean blood pressure and the systolic blood pressure measured by the blood-pressure measuring device, a minimum magnitude of the first pulse wave into an estimated diastolic blood pressure of the first portion of the subject.

According to this aspect, the first-pulse-wave detecting device detects an accurate first pulse wave from the first portion, the blood-pressure measuring device measures accurate mean and systolic blood pressure of the first portion, and the diastolic-blood-pressure estimating means estimates, based on a minimum magnitude, an area-gravity-center magnitude and a maximum magnitude of the accurate first pulse wave and the accurate mean and systolic blood pressure of the first portion, a diastolic blood pressure of the first portion. Therefore, the thus estimated diastolic blood pressure enjoys a high accuracy, and is useful in making a diagnosis. In addition, as described later, the accurate diastolic blood pressure of the first portion can be used to estimate an accurate blood pressure of a second portion different from the first portion.

According to a preferred feature of the first or second aspect of the present invention, the first-pulse-wave detecting device comprises the inflatable cuff and detects, as the first pulse wave, a pressure oscillation occurring to the cuff worn on the first portion of the subject.

According to this feature, the cuff is shared by the blood-pressure measuring device and the first-pulse-wave detecting device. Thus, the present apparatus can be produced at a lower cost. In addition, since the cuff can be worn on the subject without needing a special skill of an operator, an accurate first pulse wave can be detected independent of the degree of skill of the operator. Therefore, an accurate mean or diastolic blood pressure of the first portion can be estimated independent of the degree of skill of the operator.

According to a preferred feature of the first aspect of the present invention, the blood-pressure estimating apparatus further comprises a second-pulse-wave detecting device which detects a second pulse wave from a second portion of the subject; and a systolic-blood-pressure estimating means for converting, based on the diastolic blood pressure measured by the blood-pressure measuring device and the mean blood pressure estimated by the mean-blood-pressure estimating means, a maximum magnitude of the second pulse wave detected by the second-pulse-wave detecting device into an estimated systolic blood pressure of the second portion of the subject.

According to this feature, the systolic-blood-pressure estimating means estimates, based on the accurate second pulse wave detected by the second-pulse-wave detecting device, the accurate diastolic blood pressure measured by the blood-pressure measuring device, and the accurate mean blood pressure estimated by the mean-blood-pressure estimating means, a systolic blood pressure of the second portion of the subject. Therefore, the thus estimated systolic blood pressure of the second portion enjoys a high accuracy.

According to a preferred feature of the second aspect of the present invention, the blood-pressure estimating apparatus further comprises a second-pulse-wave detecting device which detects a second pulse wave from a second portion of the subject; and a systolic-blood-pressure estimating means for converting, based on the mean blood pressure measured by the blood-pressure measuring device and the diastolic blood pressure estimated by the diastolic-blood-pressure estimating means, a maximum magnitude of the second pulse wave detected by the second-pulse-wave detecting device into an estimated systolic blood pressure of the second portion of the subject.

According to this feature, the systolic-blood-pressure estimating means estimates, based on the accurate second pulse wave detected by the second-pulse-wave detecting device, the accurate mean blood pressure measured by the blood-pressure measuring device, and the accurate diastolic blood pressure estimated by the diastolic-blood-pressure estimating means, a systolic blood pressure of the second portion of the subject. Therefore, the thus estimated systolic blood pressure of the second portion enjoys a high accuracy.

According to another feature of the first or second aspect of the present invention, the first portion and the second portion of the subject are a brachial portion and a cervical portion of the subject, respectively.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

The above-described first portion of the living subject is, for example, a brachial portion, a femoral portion, or an ankle; and the second portion of the subject is, for example, a cervical portion, a brachial portion, a wrist, a femoral portion, or an ankle. The first and second portions may be combined in any ways so long as they differ from each other; such as the combination of a brachial portion as the first portion and a cervical portion as the second portion.

Figure 1:
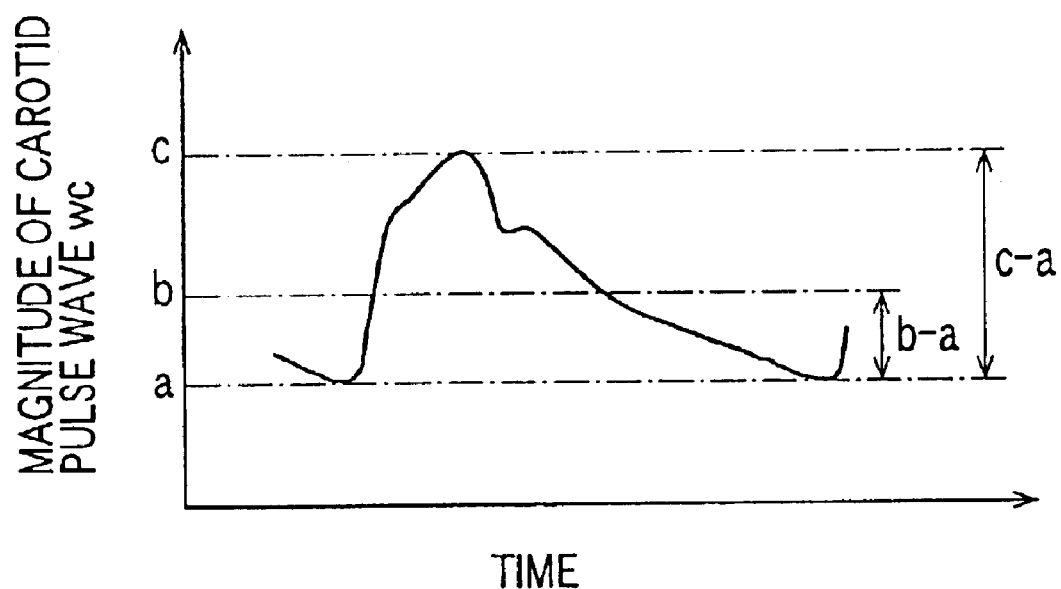
FIG. 1 is a view showing an example of a carotid pulse wave, wc.
Figure 2:
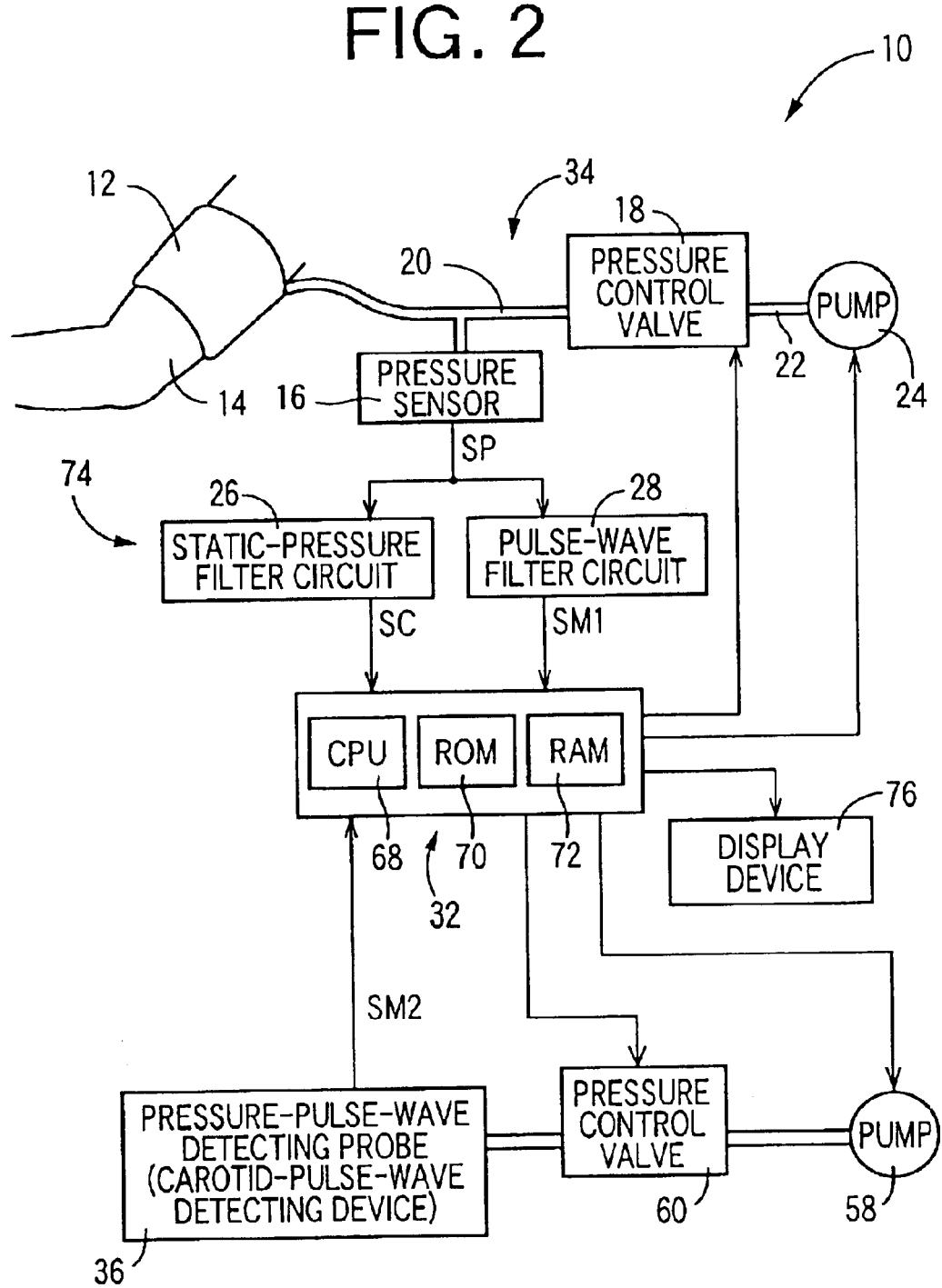
FIG. 2 is a diagrammatic view showing a circuitry of a cervical-blood-pressure determining apparatus to which the present invention is applied.

Hereinafter, there will be described an embodiment of the present invention in detail by reference to the drawings. FIG. 2 is a diagrammatic view showing a circuitry of a cervical-blood-pressure determining apparatus 10 to which the present invention is applied. The cervical-blood-pressure determining apparatus 10 also functions as a brachial-blood-pressure determining apparatus. The present apparatus 10 is used with a living subject who is taking a face-up position.

In FIG. 2, reference numeral 12 designates an inflatable cuff which includes a belt-like cloth bag and a rubber bag accommodated in the cloth bag and which is adapted to be wound around a brachial portion 14 as a first portion of the living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter, not shown. The pulse-wave filter circuit 28 includes a band-pass filter which extracts, from the pressure signal SP, a cuff-pulse-wave signal, SM1, representing a cuff pulse wave as an oscillatory component of the detected air pressure. The filter circuit 28 supplies the cuff-pulse-wave signal SM1 to the control device 32 via an A/D converter, not shown. The cuff pulse wave represented by the cuff-pulse-wave signal SM1 is a pressure oscillation that is transmitted from a brachial artery, not shown, being pressed by the cuff 12, to the cuff 12, and will be referred to as a brachial pulse wave, wb (i.e., a first pulse wave). Thus, in the cervical-blood-pressure determining apparatus 10, the cuff 12 used to detect the cuff-pulse-wave signal SM1, the pressure sensor 16, and the pulse-wave filter circuit 28 cooperate with each other to provide a brachial-pulse-wave detecting apparatus 34 (i.e., a first-pulse-wave detecting apparatus).

Figure 3:
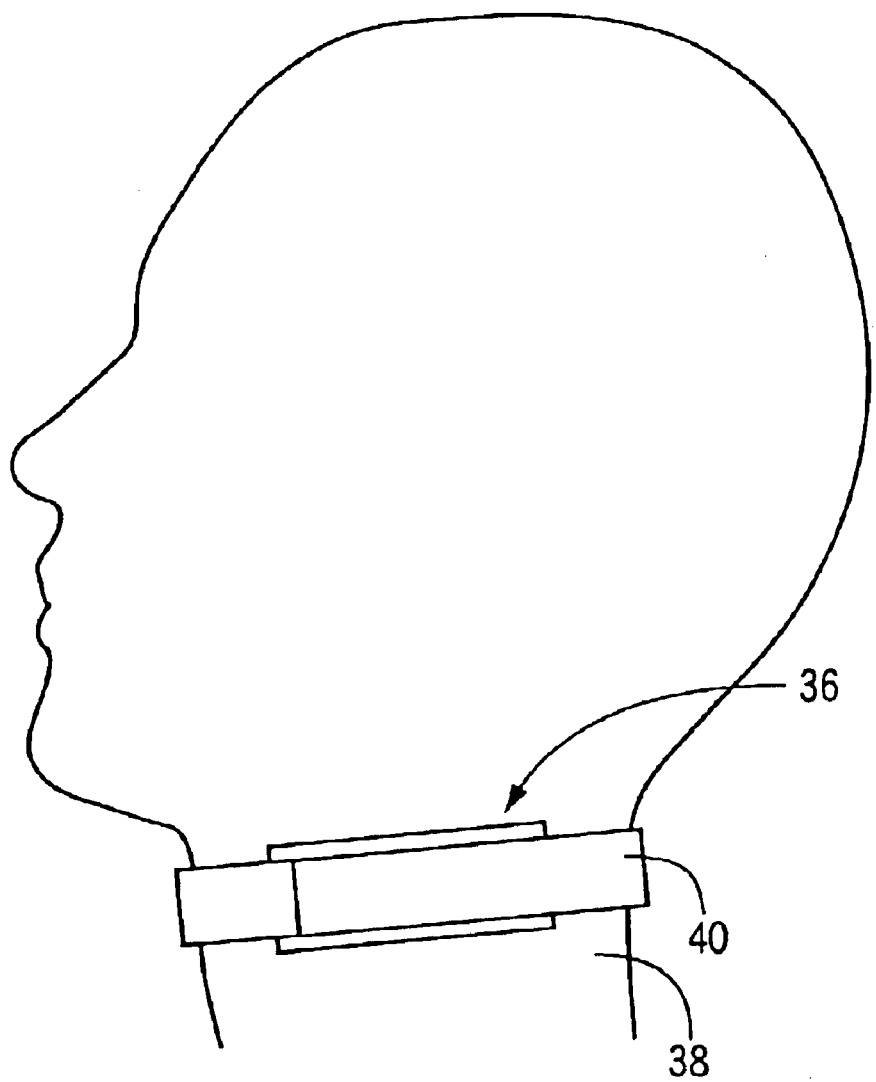
FIG. 3 is an illustrative view showing a state in which a pressure-pulse-wave detecting probe of the apparatus of FIG. 2 is worn on a neck of a living subject.
Figure 4:
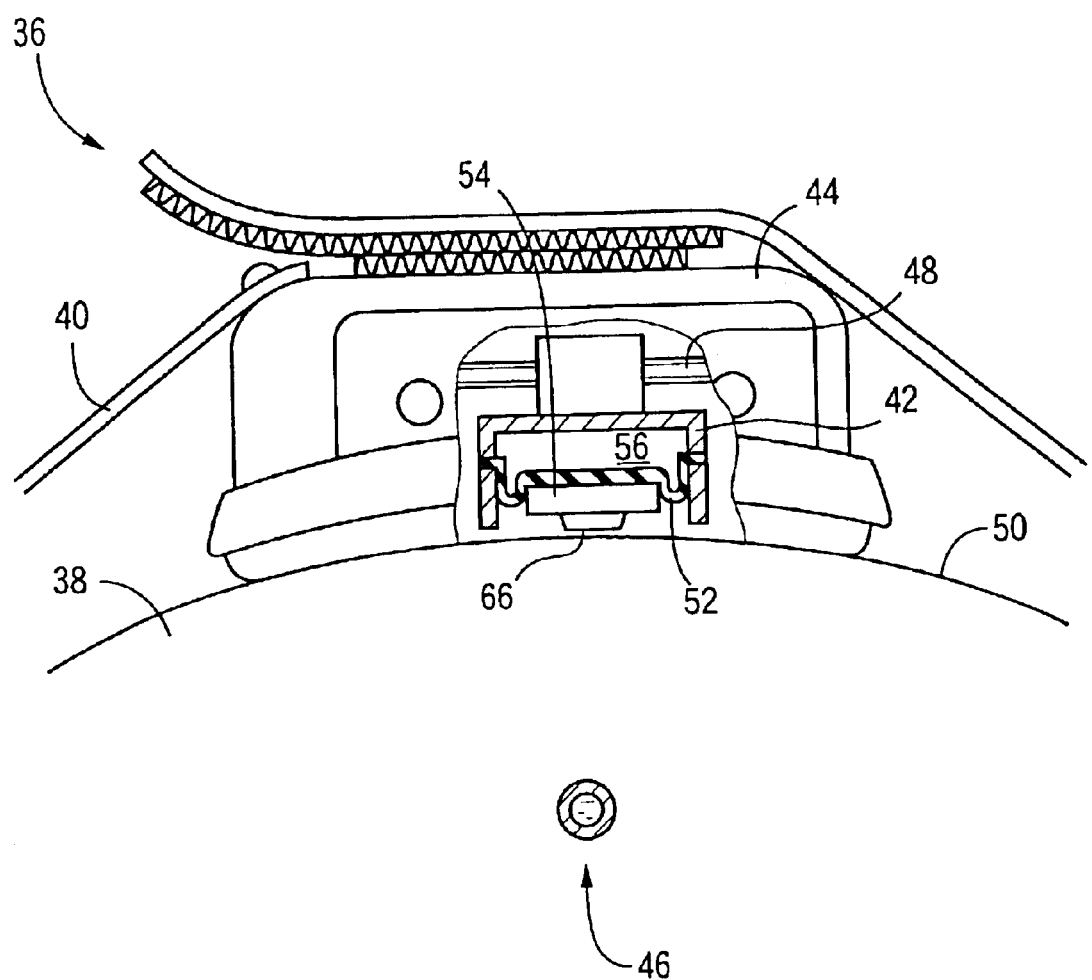
FIG. 4 is an enlarged view of the pressure-pulse-wave detecting probe of FIG. 3, a portion of the probe being cut away.

The present cervical-blood-pressure determining apparatus 10 includes a pressure-pulse-wave detecting probe 36, shown in FIG. 3, that functions as a carotid-pulse-wave detecting device (i.e., a second-pulse-wave detecting apparatus). The pressure-pulse-wave detecting probe 36 is worn on a cervical portion 38 of the subject, as shown in FIG. 3, with the help of a band 40. As shown in detail in FIG. 4, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. With the help of the band 40, the pressure-pulse-wave detecting probe 36 is detachably attached to the cervical portion 38, such that an open end of the sensor housing 42 is opposed to a body surface 50 of the cervical portion 38.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with each other to define a pressure chamber 56, which is supplied with a pressurized air from an air pump 58 via a pressure control valve 60, as shown in FIG. 2, so that the pressure-pulse-wave sensor 54 is pressed against the body surface 50 with a pressing force corresponding to the air pressure in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 5:
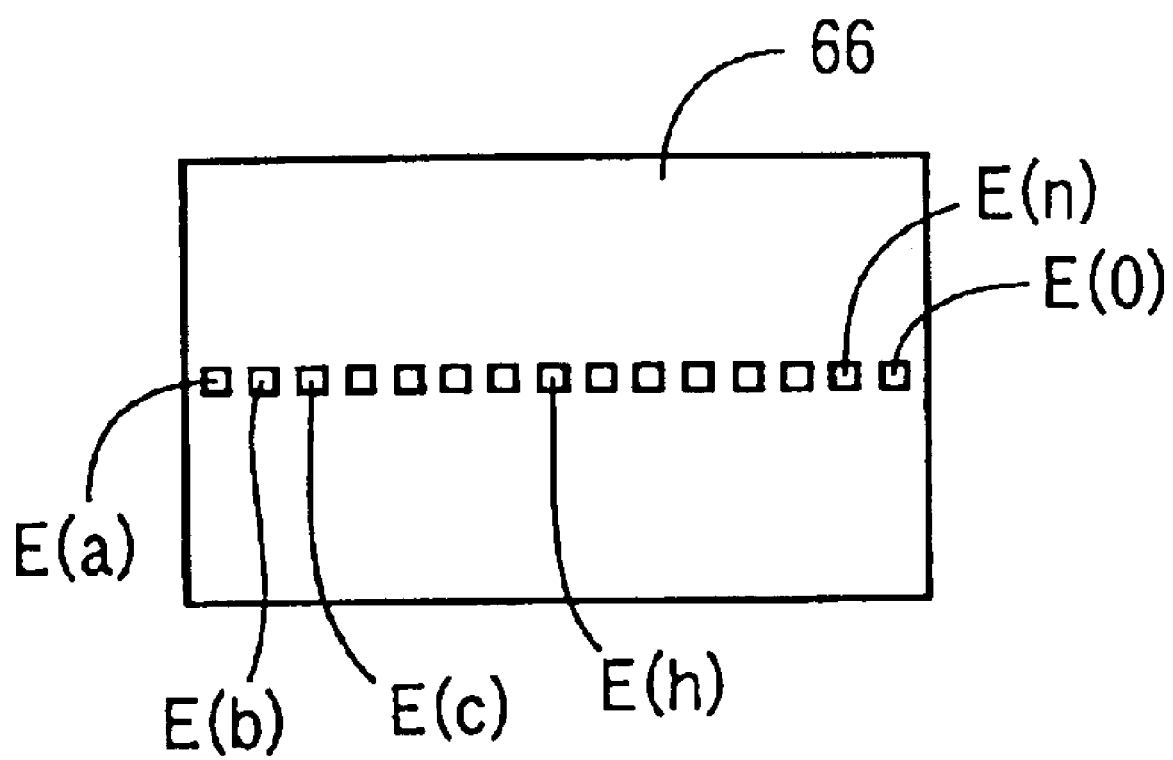
FIG. 5 is a view for explaining a state in which an array of pressure sensing elements is provided in a press surface of a pressure-pulse-wave sensor shown in FIG. 4.

The pressure-pulse-wave sensor 54 has a pressing surface 66, and a number of semiconductor pressure-sensing elements (hereinafter, referred to as the "pressure-sensing elements") E which are arranged in the pressing surface 66 at a regular interval in the widthwise direction of the carotid artery 46, i.e., in the direction of movement of the sensor 54 parallel to the feed screw 48, over a length greater than the diameter of the carotid artery 46. For example, as shown in FIG. 5, fifteen pressure-sensing elements E(a), E(b), . . . , E(o) are arranged at a regular interval of, e.g., 0.6 mm.

The pressure-pulse-wave detecting probe 36, constructed as described above, is pressed against the body surface 50 of the cervical portion 38 right above the carotid artery 46, so that the pressure-pulse-wave sensor 54 detects a pressure pulse wave (i.e., a carotid pulse wave, wc, or a second pulse wave) which is produced from the carotid artery 46 and is transmitted to the body surface 50, and supplies a pressure-pulse-wave signal SM2 representing the detected carotid pulse wave wc, to the control device 32 via an A/D converter, not shown.

The electronic control device 32 is provided by a so-called microcomputer including a CPU 68, a ROM (read only memory) 70, a RAM (random access memory) 72, and an I/O (input-and-output) port, not shown. The CPU 68 processes signals according to the control programs pre-stored in the ROM 70 by utilizing the temporary-storage function of the RAM 72, and supplies drive signals via the I/O port to the air pumps 24, 58 and the pressure control valves 18, 60 so as to control the cuff pressure PC and the air pressure in the pressure chamber 56. Moreover, the CPU 68 determines a brachial blood pressure, BBP, of the subject based on the cuff-pulse-wave signal SM1 and the cuff-pressure signal SC each supplied to the control device 32. Thus, the electronic control device 32 cooperates with a device which supplies the cuff-pulse-wave signal SM1 and the cuff-pressure signal SC to the control device 32, that is, the cuff 12, the pressure sensor 16, the pressure control valve 18, the air pump 24, the static-pressure circuit 26, and the pulse-wave filter circuit 28, to provide a brachial-blood-pressure measuring device 74 (i.e., a first-blood-pressure measuring device).

In addition, the CPU 68 determines a cervical blood pressure, CBP, of the subject based on the brachial blood pressure BBP, and the pressure-pulse-wave signal SM2 supplied from the pressure-pulse-wave detecting probe 36, and controls a display device 76 to display the thus determined cervical blood pressure CBP.

Figure 6:
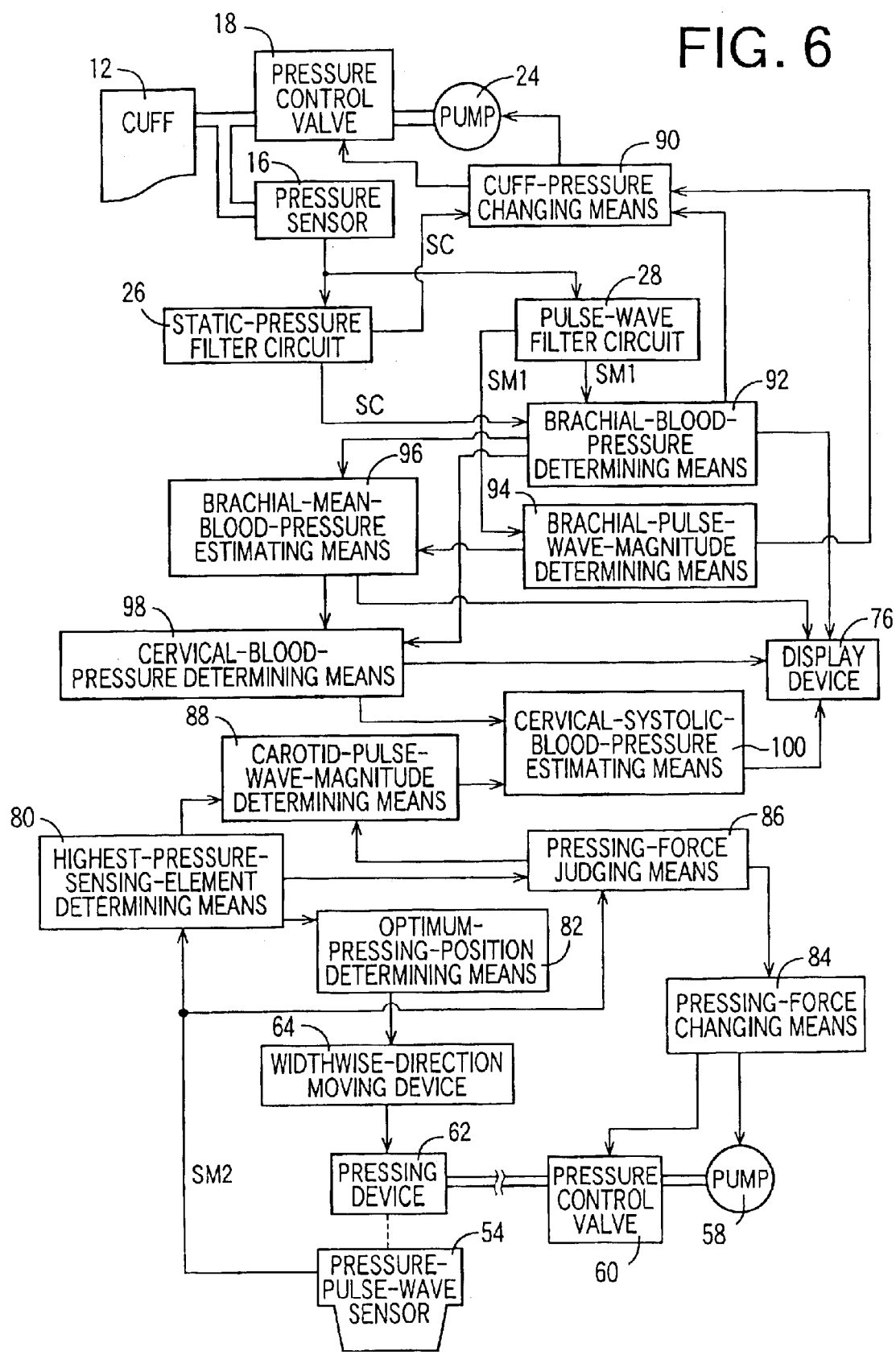
FIG. 6 is a block diagram for explaining essential control functions of an electronic control device of the apparatus of FIG. 2.

FIG. 6 is a block diagram for explaining essential control functions of the electronic control device 32 of the cervical-blood-pressure determining apparatus 10.

A highest-pressure-detecting-element determining device or means 80 determines, as a highest-pressure detecting element EM, one of the pressure sensing elements E of the pressure-pulse-wave sensor 54 that detects the highest pressure of the respective pressures detected by all the elements E. More specifically described, the determining means 80 determines the greatest one of respective magnitudes of respective peak points of the respective pressure pulse waves detected by all the elements E, and determines, as the highest-pressure detecting element EM, one of the pressure sensing elements E that provides the greatest magnitude. The highest-pressure detecting element EM is one of the elements E that is positioned right above the carotid artery 46.

An optimum-pressing-position determining device or means 82 judges whether a prescribed pressing-position changing condition is satisfied, i.e., whether the highest-pressure detecting element EM of the pressure-pulse-wave sensor 54 is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. When this pressing-position changing condition is satisfied, e.g., when the sensor 54 is initially worn on the subject, the optimum-pressing-position determining means 82 carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with a prescribed, considerably small first pressing force, HDP1. In this state, the determining means 82 judges again whether the prescribed pressing-position changing condition is satisfied. The determining means 82 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 46) to be pressed by the pressure-pulse-wave sensor 54, and may be one fourth of the diameter.

A pressing-force changing device or means 84 changes, after the optimum-pressing-position determining means 82 positions the pressure-pulse-wave sensor 54 at the optimum pressing position, a pressing force HDP (i.e., a hold-down pressure) applied by the pressing device 62 to the sensor 54, within a prescribed pressing-force range, either stepwise in response to each heartbeat of the subject or continuously at a prescribed, considerably low rate. While the pressing force HDP is changed, if a pressing-force judging device or means 86, described below, judges that a current pressing force HDP applied to the sensor 54 is appropriate, then the changing means 84 determines the current HDP as an optimum pressing force HDPO, and maintains the pressing force of the pressing device 62, at the thus determined optimum pressing force HDPO.

The pressing-force judging means 86 judges whether the current pressing force HDP applied to the pressure-pulse-wave sensor 54 is appropriate, based on the pressure pulse wave detected by the highest-pressure sensing element EM determined by the highest-pressure-sensing-element determining means 80, and the respective pressure pulse waves detected by two pressure sensing elements E (hereinafter, referred as to the comparison elements EC) that are distant from the element EM by a prescribed distance in respective directions from the element EM toward the opposite ends of the array of elements E. More specifically described, the judging means 86 determines a time difference, ΔT, between a time of detection of a prescribed point of a heartbeat-synchronous pulse of the pressure pulse wave detected by the highest-pressure sensing element EM and a time of detection of a prescribed point of a corresponding heartbeat-synchronous pulse of the pressure pulse wave detected by at least one of the two comparison elements EC, and judges whether the pressing force HDP is appropriate based on the thus determined time difference ΔT. The prescribed point of heartbeat-synchronous pulse may be a rising point, a peak point, or a dicrotic notch of the pulse.

Figure 7:
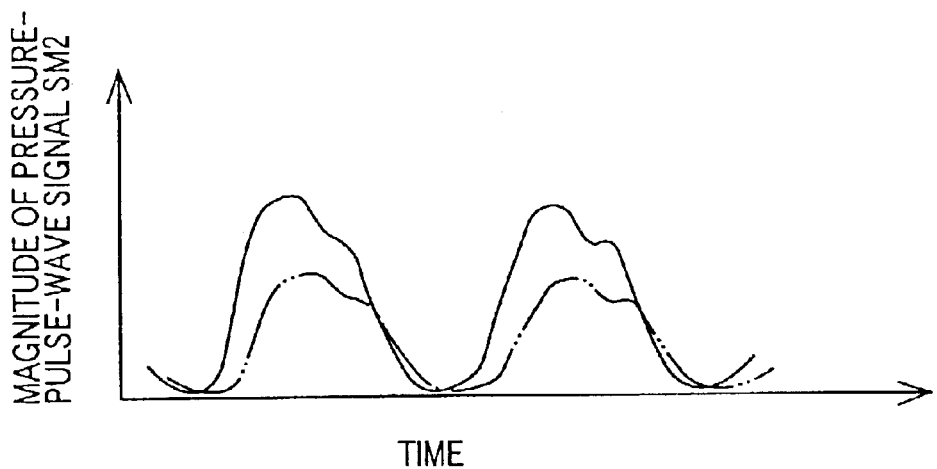
FIG. 7 is a view showing a pressure pulse wave (indicated at solid line) detected by a highest-pressure sensing element, EM, and a pressure pulse wave (indicated at two-dot-chain line) detected by a semiconductor pressure sensing element, E(x), positioned right above a non-flattened portion of the wall of a blood vessel.
Figure 8:
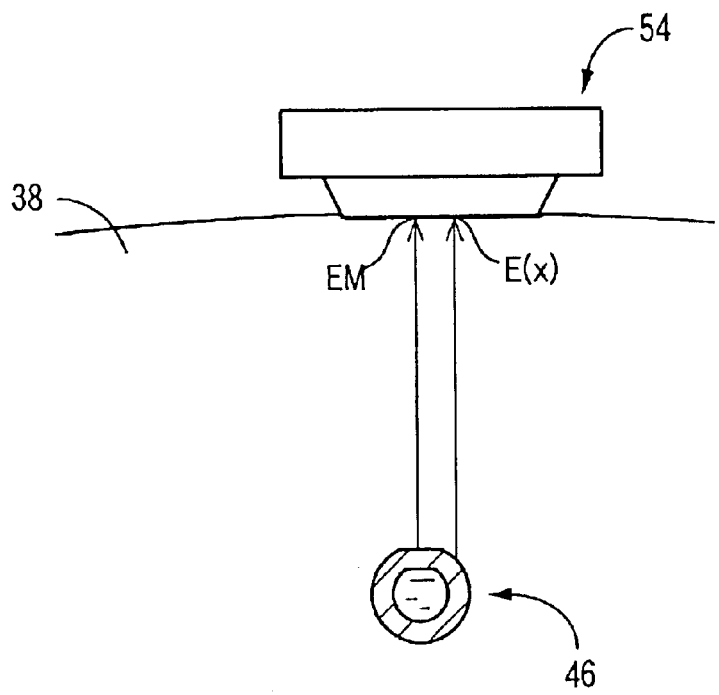
FIG. 8 is a view showing a relationship between the highest-pressure sensing element EM and the semiconductor pressure sensing element E(x), and a carotid artery.

The reason why the above-described time difference ΔT can be used to judge whether the pressing force HDP applied to the pressure-pulse-wave sensor 54 is appropriate, is as follows: FIG. 7 shows a pressure pulse wave (indicated at solid line) detected by the highest-pressure sensing element EM positioned right above a flattened portion of the wall of the carotid artery and a pressure pulse wave (indicated at two-dot-chain line) detected by a pressure sensing element, E(x), positioned right above a non-flattened portion of the arterial wall, and FIG. 8 shows a relationship between the highest-pressure sensing element EM and the pressure sensing element E(x), and the carotid artery 46. As shown in FIG. 7, a phase of a heartbeat-synchronous pulse of the pressure pulse wave detected by the pressure sensing element E(x) is delayed from a phase of a corresponding heartbeat-synchronous pulse of the pressure pulse wave detected by the highest-pressure sensing element EM, because the pressure pulse wave detected by the pressure sensing element E(x) is influenced by viscoelasticity of the non-flattened portion of the arterial wall but the pressure pulse wave detected by the highest-pressure sensing element EM is not influenced by viscoelasticity of the flattened portion of the arterial wall. Therefore, if the phase of the pressure pulse wave detected by the pressure sensing element E(x) is not delayed, or is delayed by only a short time, if any, from the phase of the pressure pulse wave detected by the highest-pressure sensing element EM, then it can be said that the pressure sensing element E(x) is positioned right above a substantially flattened portion of the wall of the carotid artery (or that a portion of the wall of the carotid artery is substantially flattened by the pressing force).

Therefore, if the time difference ΔT between the time of detection of the prescribed point of the pressure pulse wave detected by the highest-pressure sensing element EM and the time of detection of the prescribed point of the pressure pulse wave detected by at least one of the two comparison elements EC, is smaller than an upper-limit time, TH1, that is experimentally determined in advance, then it can be judged that the carotid artery 46 is in the state in which a portion of the wall of the artery is substantially flattened by the pressing force HDP applied to the pressure-pulse-wave sensor 54, that is, that the current pressing force HDP applied to the sensor 54 is appropriate. The distance between the highest-pressure sensing element EM and each of the two comparison elements EC is so prescribed as to be shorter than the diameter of the artery (e.g., equal to one fifth of the diameter of the artery).

A carotid-pulse-wave-magnitude determining device or means 88 determines a minimum magnitude, a, an area-gravity-center magnitude, b, and a maximum magnitude, c, of a unit length of the carotid pulse wave wc represented by the pressure-pulse-wave signal SM2 supplied from the highest-pressure sensing element EM in the state in which the pressing-force judging means 86 is judging that the current pressing force applied to the pressure-pulse-wave sensor 54 is appropriate. The unit length of the carotid pulse wave may be prescribed either on a heartbeat basis, such as a length corresponding to one heartbeat or a prescribed number of heartbeats, or on a time basis, such as a length equal to several seconds or several tens of seconds. The area-gravity-center magnitude b is an average magnitude of one-heartbeat length of the carotid pulse wave wc that may be obtained by integrating the magnitude of one-heartbeat length of the carotid pulse wave wc and dividing the integral value by a period, T, of the one-heartbeat length of the pulse wave wc. However, the determining means 88 may be modified to determine respective minimum magnitudes a, respective area-gravity-center magnitudes b, and respective maximum magnitudes c of a plurality of unit lengths of the carotid pulse wave wc, and additionally determine respective averages of the minimum magnitudes a, the area-gravity-center magnitudes b, and the maximum magnitudes c.

A cuff-pressure changing device or means 90 operates, according to a command signal supplied from a brachial-blood-pressure determining device or means 92 or a brachial-pulse-wave-magnitude determining device or means 94, each described later, and based on the cuff-pressure signal SC supplied from the static-pressure filter circuit 26, the pressure control valve 18 and the air pump 24 so as to change the cuff pressure PC as follows: When the changing means 90 receives a command signal supplied from the brachial-blood-pressure determining means 92, the changing means 90 quickly increases the cuff pressure PC up to a prescribed target pressure (e.g., 180 mmHg) that would be higher than a systolic blood pressure BBP(SYS) of the brachial portion of the subject and, subsequently, slowly decreases the cuff pressure at a low rate of, e.g., 2 or 3 mmHg/sec. After a brachial blood pressure BBP of the subject is determined, the changing means 90 releases the cuff pressure PC down to an atmospheric pressure. Meanwhile, when the changing means 90 receives a command signal supplied from the brachial-pulse-wave-magnitude determining means 94, the changing means 90 changes and keeps the cuff pressure PC to and at a prescribed pulse-wave detection pressure.

The pulse-wave detection pressure is so prescribed as to assure that a waveform of the cuff-pulse-wave signal SM1 supplied from the pulse-wave filter circuit 28 is substantially identical with a waveform of a brachial pulse wave wb that is obtained in a state in which the brachial portion of the subject is not pressed by the cuff. If the cuff pressure PC is higher than a diastolic blood pressure BBP(DIA) of the brachial portion of the subject, the waveform of the cuff-pulse-wave signal SM1 is deformed by the pressing of the cuff 12 and accordingly is not identical with that of the brachial pulse wave wb obtained in the state in which the brachial portion is not pressed by the cuff. Therefore, the pulse-wave detection pressure is so prescribed as to be a fixed pressure that would be lower than the brachial diastolic blood pressure BBP(DIA), or as to be lower than an actually measured brachial diastolic blood pressure BBP(DIA). In the latter case, the pulse-wave detection pressure may be determined by subtracting, from the actually measured brachial diastolic blood pressure BBP(DIA), a prescribed pressure, α, that is sufficiently smaller than the diastolic blood pressure BBP(DIA); such as 10 mmHg or 20 mmHg.

The brachial-blood-pressure determining device or means 92 as a first blood-pressure determining device or means determines, based on the cuff-pressure signal SC continuously supplied from the static-pressure filter circuit 26, and the cuff-pulse-wave signal SM1 continuously supplied from the pulse-wave filter circuit 28, each during the slow decreasing of the cuff pressure PC under the control of the cuff-pressure changing means 90, a systolic blood pressure BBP(SYS) and a diastolic blood pressure BBP(DIA) of the brachial portion of the subject (i.e., first blood pressure values of the subject), according to a well-known oscillometric algorithm. According to the oscillometric algorithm, the determining means 92 determines an envelope of respective amplitudes, A, of respective heartbeat-synchronous pulses of the brachial pulse wave wb, and determines, as the brachial systolic blood pressure BBP(SYS), a value of the cuff pressure PC at the time of detection of a rising point of the envelope and additionally determines, as the brachial diastolic blood pressure BBP(DIA), a value of the cuff pressure PC at the time of detection of a falling point of the envelope (i.e., an inflection point of the envelope). An amplitude A of a heartbeat-synchronous pulse of the brachial pulse wave wb is defined as a difference between a maximum magnitude and a minimum magnitude of the pulse. The determining means 92 operates the display device 76 to display the thus determined brachial systolic and diastolic blood pressure values BBP(SYS), BBP(DIA).

The brachial-pulse-wave-magnitude determining device or means 94 determines a minimum magnitude, d, an area-gravity-center magnitude, e, and a maximum magnitude, f, of a unit length of the brachial pulse wave wb represented by the cuff-pulse-wave signal SM1 supplied from the pulse-wave filter circuit 28 in the state in which the cuff-pressure changing means 90 is keeping the cuff pressure PC at the pulse-wave detection pressure. Here, each of the unit length and the area-gravity-center magnitude has the same definition as described above with respect to the carotid-pulse-wave-magnitude determining means 88.

Figure 9:
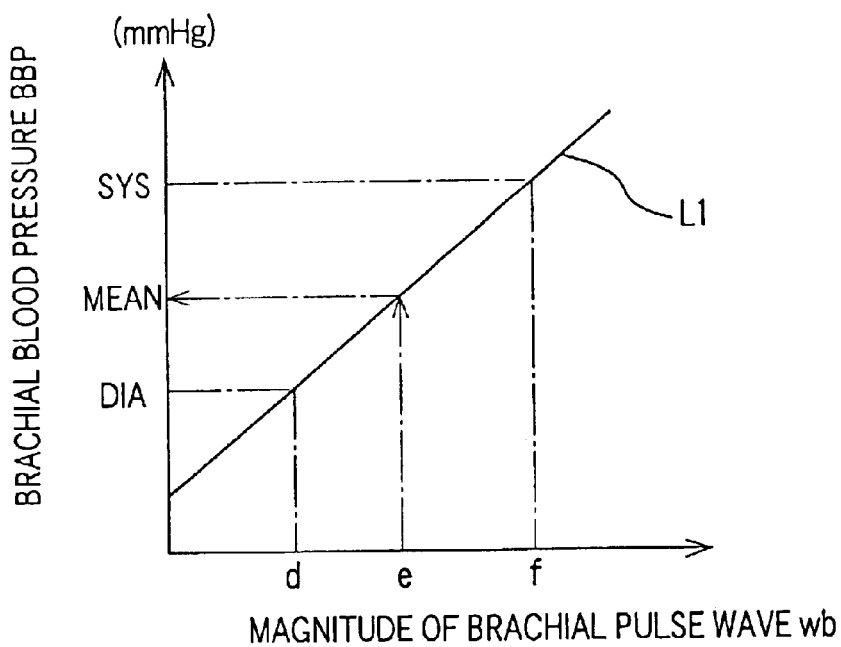
FIG. 9 is a view showing a relationship between magnitude of brachial pulse wave, wb, and brachial blood pressure, BBP.

A brachial-mean-blood-pressure estimating device or means 96 as a first-mean-blood-pressure estimating means estimates a mean blood pressure BBP(MEAN) of the brachial portion of the subject, based on the brachial systolic and diastolic blood pressure values BBP(SYS), BBP(DIA) determined by the brachial-blood-pressure determining means 92, and the minimum magnitude d, the area-gravity-center magnitude e, and the maximum magnitude f of the brachial pulse wave wb determined by the brachial-pulse-wave-magnitude determining means 94. More specifically described, since the minimum magnitude d of the brachial pulse wave wb corresponds to the brachial diastolic blood pressure BBP(DIA), and the maximum magnitude f of the brachial pulse wave wb corresponds to the brachial systolic blood pressure BBP(SYS), the estimating means 96 determines a straight line, L1, representing a relationship between magnitude of brachial pulse wave wb and brachial blood pressure BBP, shown in FIG. 9, based on the brachial systolic and diastolic blood pressure values BBP(SYS), BBP(DIA) determined by the brachial-blood-pressure determining means 92 and the minimum and maximum magnitudes d, f of the brachial pulse wave wb determined by the brachial-pulse-wave-magnitude determining means 94. In addition, the estimating means 96 estimates the brachial mean blood pressure BBP(MEAN), based on the straight line L1 and the area-gravity-center magnitude e of the brachial pulse wave wb. However, it is not essentially needed to determine the straight line L1. In the latter case, the brachial mean blood pressure BBP(MEAN) may be determined according to a proportional relationship represented by the following Expression 2, the following Expression 3 that is derived from Expression 2, or a different proportional relationship equivalent to Expression 2:

$$f-d:e-d=BBP(SYS)-BBP(DIA):BBP(MEAN)-BBP(DIA) \quad \text{(Expression 2)}$$

$$BBP(MEAN)=\{(e-d)\times BBP(SYS)-(e-f)\times BBP(DIA)\}/(f-d) \quad \text{(Expression 3)}$$

The estimating means 96 operates the display device 76 to display the thus estimated brachial mean blood pressure BBP(MEAN).

A cervical-blood-pressure determining device or means 98 as a second-blood-pressure determining means determines the brachial diastolic blood pressure BBP(DIA) as determined by the brachial-blood-pressure determining means 92, as a diastolic blood pressure CBP(DIA) of the cervical portion of the subject, i.e., a second diastolic blood pressure, and additionally determines the brachial mean blood pressure BBP(MEAN) as estimated by the brachial-mean-blood-pressure estimating means 96, as a mean blood pressure CBP(MEAN) of the cervical portion of the subject, i.e., a second mean blood pressure. Moreover, the determining means 98 operates the display device 76 to display the thus determined cervical diastolic and mean blood pressure CBP(DIA), CBP(MEAN).

Figure 10:
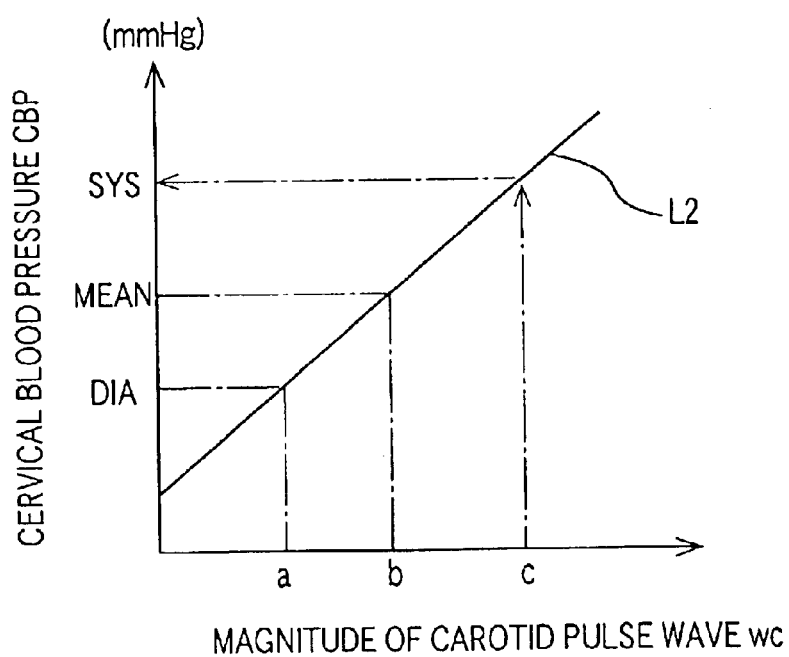
FIG. 10 is a view showing a relationship between magnitude of carotid pulse wave wc, and neck blood pressure, CBP.

A cervical-systolic-blood-pressure estimating device or means 100 as a second-systolic-blood-pressure estimating means estimates a systolic blood pressure CBP(SYS) of the cervical portion of the subject, i.e., a second systolic blood pressure of the subject, based on the cervical mean and diastolic blood pressure values CBP(MEAN), CBP(DIA) determined by the cervical-blood-pressure determining means 98, and the minimum magnitude a, the area-gravity-center magnitude b, and the maximum magnitude c of the carotid pulse wave wc determined by the carotid-pulse-wave-magnitude determining means 88. More specifically described, since the minimum magnitude a of the carotid pulse wave wc corresponds to the cervical diastolic blood pressure CBP(DIA), and the area-gravity-center magnitude b of the carotid pulse wave wc corresponds to the cervical mean blood pressure CBP(MEAN), the estimating means 100 determines a straight line, L2, representing a relationship between magnitude of carotid pulse wave wc and cervical blood pressure CBP, shown in FIG. 10, based on the cervical diastolic and mean blood pressure values CBP(DIA), CBP(MEAN) determined by the cervical-blood-pressure determining means 98 and the minimum and area-gravity-center magnitudes a, b of the carotid pulse wave wc determined by the carotid-pulse-wave-magnitude determining means 88. In addition, the estimating means 100 estimates the cervical systolic blood pressure CBP(SYS), based on the straight line L2 and the maximum magnitude c of the carotid pulse wave wc. However, it is not essentially needed to determine the straight line L2. In the latter case, the cervical systolic blood pressure CBP(SYS) may be determined according to the proportional relationship represented by the previously-explained Expression 1, the following Expression 4 that is derived from Expression 1, or a different proportional relationship equivalent to Expression 1:

$$CBP(SYS)=\{(c-a)\times CBP(MEAN)-(c-b)\times CBP(DIA)\}/(b-a) \quad \text{(Expression 4)}$$

The estimating means 100 operates the display device 76 to display the thus estimated cervical systolic blood pressure CBP(SYS).

Figure 11:
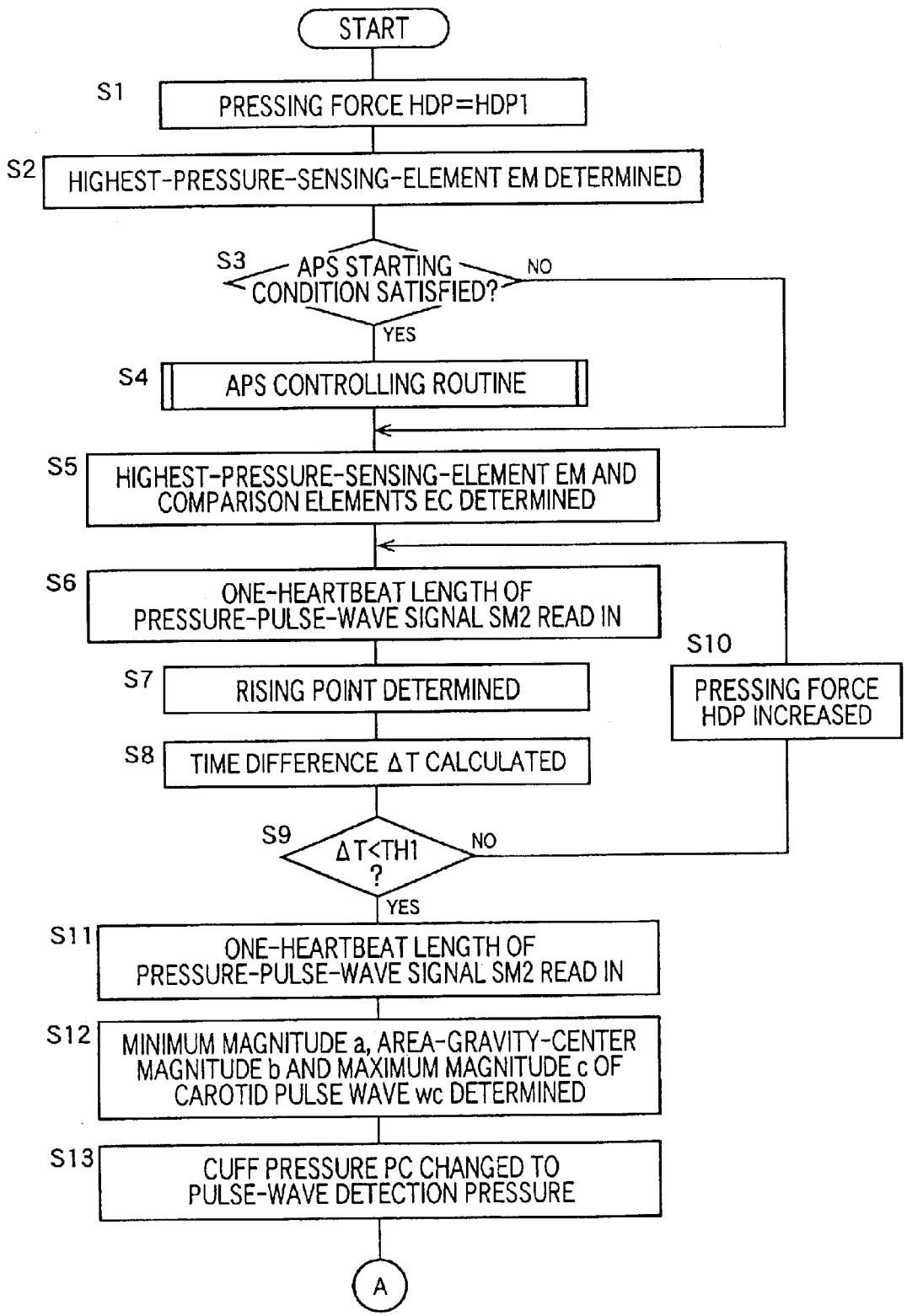
FIG. 11 is a flow chart for explaining more concretely a portion of the control functions of a CPU (central processing unit) of the electronic control device, shown in FIG. 6.
Figure 12:
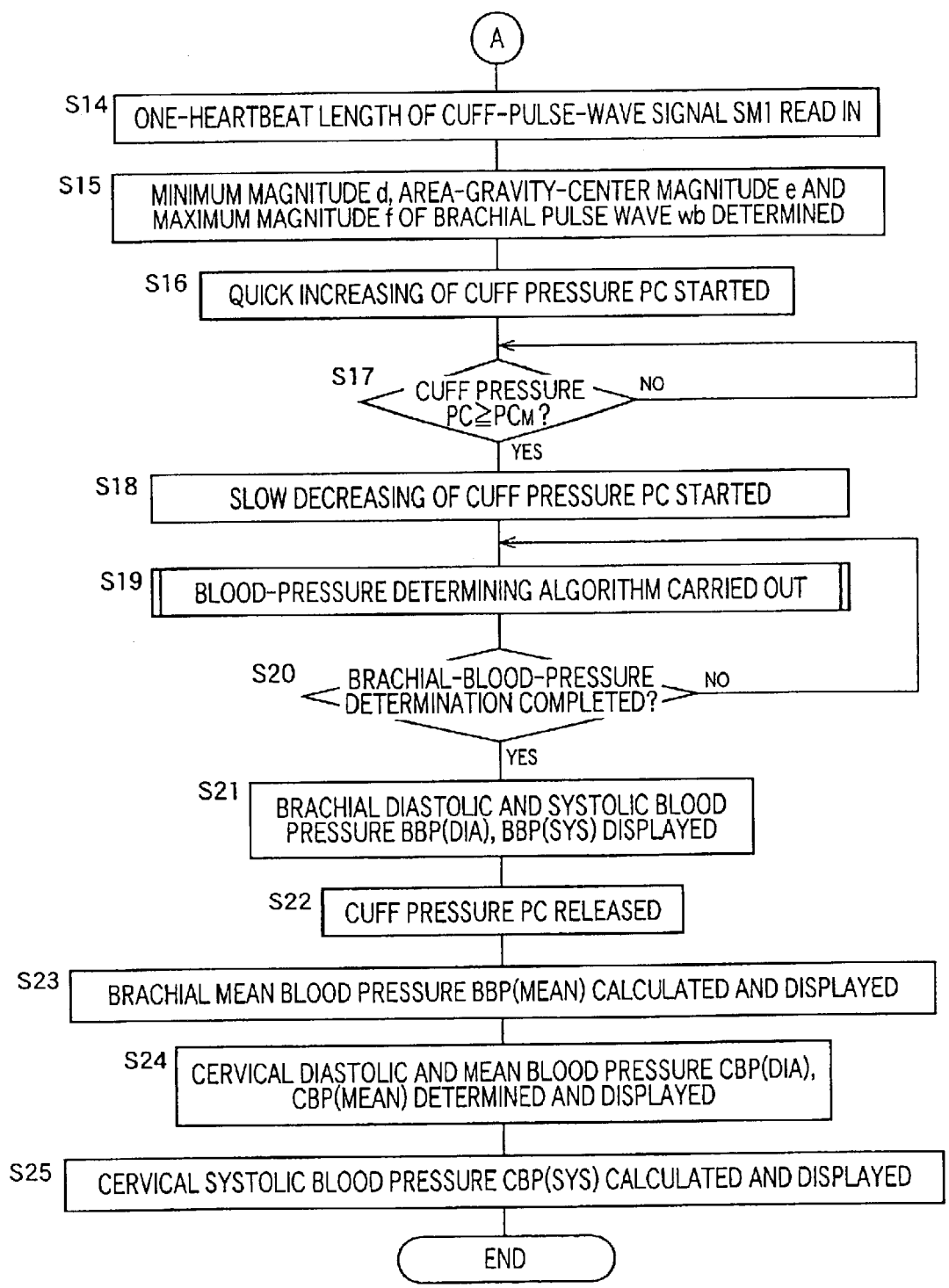
FIG. 12 is a flow chart for explaining more concretely another portion of the control functions of the CPU, shown in FIG. 6.

FIGS. 11 and 12 are flow charts representing the control functions of the CPU 68, shown in the diagrammatic view of FIG. 6.

In FIG. 11, first, the CPU carries out Step S1 (hereinafter, the term "Step" is omitted) corresponding to the pressing-force changing means 84. At S1, the CPU operates the pressing device 62 to change the pressure in the pressure chamber 56 so that the pressing force HDP applied to the pressure-pulse-wave sensor 54 is changed to the prescribed first pressing force HDP1. The first pressing force HDP1 is so prescribed as to be sufficiently smaller than an average optimum pressing force HDPO, and is so experimentally determined, in advance, as to assure that the CPU can accurately determine respective magnitudes of respective peak points of the respective pressure pulse waves detected by the respective pressure sensing elements E, based on the respective pressure-pulse-wave signals SM2 supplied from the elements E.

Subsequently, the control of the CPU goes to S2 corresponding to the highest-pressure sensing element determining means 80. At S2, the CPU reads in respective one-heartbeat lengths of the respective pressure-pulse-wave signals SM2 supplied from the pressure sensing elements E, and determines respective peak points of the respective pressure pulse waves represented by the respective one-heartbeat lengths of the pressure-pulse-wave signals SM2, determines respective magnitudes of the thus determined peak points, and determines one of the pressure sensing elements E that provides the greatest peak magnitude, as a highest-pressure sensing element EM.

Then, the control goes to S3 and S4 corresponding to the optimum-pressing-position determining means 82. First, at S3, the CPU judges whether a prescribed pressing-position changing condition (i.e, an APS starting condition) is satisfied, i.e., whether the highest-pressure sensing element EM is positioned in one of the prescribed opposite end portions of the array of pressure-sensing elements E. If a negative judgment is made at S3, the control jumps to S5 and the following steps, described later.

On the other hand, if a positive judgment is made at S3, that is, if the position of the pressure-pulse-wave sensor 54 relative to the carotid artery 46 is not appropriate, the control goes to S4 to carry out an APS controlling routine. More specifically described, the highest-pressure sensing element EM is moved to an optimum pressing position where the highest-pressure sensing element EM is located at substantially the middle of the array of pressure sensing elements E, in such a manner that after the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with the above-described first pressing force HDP1. In this state, the CPU judges again whether the highest-pressure sensing element EM is positioned in a prescribed middle portion of the array of elements E. The CPU repeats carrying out those operation and judgment till a positive judgment is made at S4.

After the pressure-pulse-wave sensor 54 is positioned at the optimum pressing position, the control goes to S5 corresponding to the highest-pressure sensing element determining means 80. At S5, the CPU determines a highest-pressure sensing element EM in the same manner as employed at S2, and additionally determines two pressure sensing elements E on both sides of the highest-pressure sensing element EM as comparison elements EC.

Subsequently, the control goes to S6 through S9 corresponding to the pressing-force judging means 86. First, at S6, the CPU reads in, at a prescribed sampling period, Ts, the respective pressure-pulse-wave signals SM2 supplied from the pressure sensing elements E, and obtains respective one-heartbeat lengths of the respective signals SM2. Subsequently, at S7, the CPU determines, as a rising point, a point where a rate of increase of amplitude of the pressure pulse wave represented by the pressure-pulse-wave signal SM2 supplied from the highest-pressure sensing element EM, read in at S6, takes a maximum value and additionally determines, as a reference time, Tst, a time of detection of the rising point. In the same manner, the CPU determines respective rising points with respect to the respective pressure-pulse-wave signals SM2 supplied from the two comparison elements EC, and determines, as respective comparison times Tco, respective times of detection of those rising points.

Subsequently, at S8, the CPU calculates a time difference, ΔT, between the reference time Tst determined at S7 and each of the two comparison times Tco. Each of the two time-difference values ΔT is obtained as an absolute value. Subsequently, at S9, the CPU judges whether each of the two time differences ΔT calculated at S8 is shorter than an upper-limit time, TH1, that is so prescribed as to be from one fold to three folds longer than the sampling period Ts. Since the two comparison elements EC are determined and the two time differences ΔT are calculated, it is preferred, at S9, to judge whether each of the two time differences ΔT is smaller than the upper-limit time TH1. However, S9 may be modified such that the CPU judges whether at least one of the two time differences ΔT is smaller than the upper-limit time TH1.

If a negative judgment is made at S9, the control goes to S10 corresponding to the pressing-force changing means 84. At S10, the CPU operates the pressing device 62 to press the pressure-pulse-wave sensor 54 with the pressing force HDP increased by a prescribed amount, and then the control goes back to S6 and the following steps. Meanwhile, if a positive judgment is made at S9, that is, if the pressing force HDP applied to the sensor 54 is appropriate, the control goes to S11 and S12 corresponding to the carotid-pulse-wave-magnitude determining means 88. First, at S11, the CPU reads in, at the sampling period Ts, the pressure-pulse-wave signal SM2 supplied from the highest-pressure sensing element EM and obtains a one-heartbeat length of the signal SM2. Subsequently, at S12, the CPU determines a minimum magnitude a and a maximum magnitude c of a heartbeat-synchronous pulse of the carotid pulse wave wc, represented by the pressure-pulse-wave signal SM2 read in at S11, and additionally determines, as an area-gravity-center magnitude b of the carotid pulse wave wc, an average magnitude of the heartbeat-synchronous pulse of the carotid pulse wave wc, represented by the pressure-pulse-wave signal SM2 read in at the sampling period Ts at S11.

Subsequently, at S13, the CPU starts the air pump 24 and operates the pressure control valve 18 so as to change the cuff pressure PC to the pulse-wave detection pressure equal to, e.g., 50 mmHg.

Next, S14 and the following steps shown in FIG. 12 will be explained. S14 and S15 correspond to the brachial-pulse-wave-magnitude determining means 94. At S14, the CPU reads in, at the sampling period Ts, the cuff-pulse-wave signal SM1 supplied from the pulse-wave filter circuit 28 in the state in which the cuff pressure PC is kept at the pulse-wave detection pressure, and obtains a one-heartbeat length of the signal SM1. Subsequently, at S15, the CPU determines a minimum magnitude d and a maximum magnitude f of a heartbeat-synchronous pulse of the brachial pulse wave wb, represented by the cuff-pulse-wave signal SM1 read in at S14, and additionally determines, as an area-gravity-center magnitude e of the brachial pulse wave wb, an average magnitude of the heartbeat-synchronous pulse of the brachial pulse wave wb, represented by the cuff-pulse-wave signal SM1 read in at the sampling period Ts at S14.

Subsequently, at S16, the CPU operates the pressure control valve 18 so as to start quickly increasing the cuff pressure PC. Subsequently, at S17, the CPU judges whether the cuff pressure PC has exceeded a prescribed target pressure $PC_M$ equal to 180 mmHg. S17 is repeated until a positive judgment is made, while the cuff pressure PC is quickly increased. Meanwhile, if a positive judgment is made at S17, the control goes to S18 to stop the air pump 24 and operate the pressure control valve 18 so as to start slowly decreasing the cuff pressure PC at a rate of about 3 mmHg/sec.

Then, the control goes to S19 through S21 corresponding to the brachial-blood-pressure determining means 92. At S19, the CPU determines, based on change of respective amplitudes of successive heartbeat-synchronous pulses of the brachia pulse wave wb represented by the cuff-pulse-wave signal SM1 continuously obtained during the slow decreasing of the cuff pressure PC, a systolic blood pressure BBP(SYS) and a diastolic blood pressure BBP(DIA) of the brachial portion of the subject, according to well-known oscillometric blood-pressure determining algorithm. Then, at S20, the CPU judges whether the determination of the brachial blood-pressure values BBP have been completed at S19.

S19 is repeated until a positive judgment is made at S20, while the blood-pressure determining algorithm is continued. Meanwhile, if a positive judgment is made at S20, the control goes to S21 to operate the display device 76 to display the brachial systolic and diastolic blood-pressure values BBP(SYS), BBP(DIA) determined according to the blood-pressure determining algorithm. Then, at S22, the CPU operates the pressure control valve 18 to decrease the cuff pressure PC to an atmospheric pressure. In the present flow chart, S13, S16 through S18 and S22 correspond to the cuff-pressure changing means 90.

Next, the control goes to S23 corresponding to the brachial-mean-blood-pressure estimating means 96. At S23, the CPU calculates a brachial mean blood pressure BBP (MEAN) of the subject by replacing the above-described Expression 3 with the minimum magnitude d, area-gravity-center magnitude e, and maximum magnitude f of the brachial pulse wave wb, determined at S15, and the brachial diastolic and systolic blood pressure BBP(DIA), BBP(SYS), determined at S19, and additionally operates the display device 76 to display the thus calculated brachial mean blood pressure BBP(MEAN).

Subsequently, the control goes to S24 corresponding to the cervical-blood-pressure determining means 98. At S24, the CPU determines the brachial diastolic blood pressure BBP(DIA), determined at S19, as a cervical diastolic blood pressure CBP(DIA), without any modifications, determines the brachial mean blood pressure BBP(MEAN), calculated at S23, as a cervical mean blood pressure CBP(MEAN), without any modifications, and operates the display device 76 to display the thus determined cervical diastolic and mean blood pressure CBP(DIA), CBP(MEAN).

Subsequently, the control goes to S25 corresponding to the cervical-systolic-blood-pressure estimating means 100. At S25, the CPU calculates a cervical systolic blood pressure CBP(SYS) of the subject by replacing the above-described Expression 4 with the minimum magnitude a, area-gravity-center magnitude b, and maximum magnitude c of the carotid pulse wave wc, determined at S12, and the cervical diastolic and mean blood pressure CBP(DIA), CBP (MEAN), determined at S24, and additionally operates the display device 76 to display the thus calculated cervical systolic blood pressure CBP(SYS).

In the above-described embodiment, the brachial-pulse-wave detecting device 34 detects an accurate brachial pulse wave wb, the brachial-blood-pressure measuring device 74 measures accurate brachial diastolic and systolic blood pressure BBP(DIA), BBP(SYS), and the brachia-mean-blood-pressure estimating means 96 (S23) estimates, based on the minimum magnitude d, area-gravity-center magnitude e, and maximum magnitude f of the accurate brachial pulse wave wb and the accurate diastolic and systolic blood pressure BBP(DIA), BBP(SYS), an accurate brachial mean blood pressure BBP(MEAN). Therefore, the thus estimated brachial mean blood pressure BBP(MEAN) enjoys a high accuracy.

Also, in the above-described embodiment, the cuff 12 is shared by the brachial-blood-pressure measuring device 74 and the brachial-pulse-wave detecting device 34. Thus, the cervical-blood-pressure determining apparatus 10 can be produced at a lower cost. In addition, since the cuff 12 can be worn on the subject without needing a special skill of an operator, an accurate brachial pulse wave wb can be detected independent of the degree of skill of the operator. Therefore, an accurate brachial mean blood pressure BBP(MEAN) can be estimated independent of the degree of skill of the operator.

Also, in the above-described embodiment, the cervical-systolic-blood-pressure estimating means 100 (S25) estimates, based on the accurate carotid pulse wave wc detected by the pressure-pulse-wave detecting probe 36, the accurate brachial diastolic blood pressure BBP(DIA) measured by the brachial-blood-pressure determining means 92 (S19 through S21), and the accurate brachial mean blood pressure BBP(MEAN) estimated by the brachial-mean-blood-pressure estimating means 96 (S23), a systolic blood pressure CBP(SYS) of the cervical portion of the subject. Therefore, the thus estimated cervical systolic blood pressure CBP(SYS) enjoys a high accuracy.

While the present invention has been described in its preferred embodiment by reference to the drawings, it is to be understood that the invention may otherwise be embodied.

For example, in the above-described embodiment, the brachial-pulse-wave detecting device 34 detects, as the brachial pulse wave wb, the pressure oscillation transmitted to the cuff 12. However, it is possible to employ a brachial-pulse-wave detecting device that includes a pressure sensor identical with the pressure-pulse-wave sensor 54 and presses, with a prescribed pressing force, the sensor 54 against the brachial portion 14 so as to detect a brachial pulse wave wb.

Also, in the above-described embodiment, the blood-pressure measuring device 74 is of the oscillometric type. However, it is possible to employ a blood-pressure measuring device of a so-called K-sound type that measures blood pressure values based on cuff-pressure values when Korotkoff sounds are first and last detected. Otherwise, it is possible to employ a blood-pressure measuring device of a supersonic-Doppler type that includes supersonic-wave emitter and receiver adapted to be placed right above an artery, and measures blood-pressure values by detecting opening and closing of the artery when a pressure applied to the artery is changed.

Also, in the above-described embodiment, first, the carotid pulse wave wc is detected, subsequently the brachial pulse wave wb is detected, and then the brachial blood pressure BBP is measured. However, the order in which the carotid pulse wave wc is detected, the brachial pulse wave wb is detected, and the brachial blood pressure BBP is measured, is not limited to the order employed in the illustrated embodiment. For example, the brachial blood pressure BBP may be measured before the detection of the brachial pulse wave wb. In the latter case, it is possible to determine, based on an actually measured brachial diastolic blood pressure BBP(DIA), a pulse-wave detection pressure that is to be used for detecting a brachial pulse wave wb.

Also, in the above-described embodiment, the display device 76 displays the brachial diastolic blood pressure BBP(DIA), the brachial mean blood pressure BBP(MEAN), the brachial systolic blood pressure BBP(SYS), the cervical diastolic blood pressure CBP(DIA), the cervical mean blood pressure CBP(MEAN), and the cervical systolic blood pressure CBP(SYS). In addition to those blood-pressure values, or in place of a portion of those values, the display device 76 may display a brachial pulse pressure and/or a cervical pulse pressure. A pulse pressure is defined as a difference between a systolic blood pressure and a diastolic blood pressure. Otherwise, the display device 76 may display a waveform of the carotid pulse wave wc.

The cervical-blood-pressure determining apparatus 10 may be so modified as to obtain pulse-wave-propagation-velocity-related information that is related to a velocity at which a pulse wave propagates between two portions of the subject; such as a pulse-wave propagation velocity or a pulse-wave propagation time. In this modified embodiment, the display device 76 may display the obtained pulse-wave-propagation-velocity-related information.

Also, in the above-described embodiment, the brachial-blood-pressure determining means 92 determines the brachial diastolic blood pressure BBP(DIA) based on the cuff-pulse-wave signal SM1, and the brachial-systolic-blood-pressure estimating means 96 determines the brachial systolic blood pressure BBP(SYS) based on the brachial diastolic blood pressure BBP(DIA), etc. However, conversely, it is possible to determine a brachial mean blood pressure BBP(MEAN) based on the cuff-pulse-wave signal SM1, and estimate a brachial diastolic blood pressure BBP(DIA) based on the brachial mean blood pressure BBP(MEAN), etc.

Figure 13:
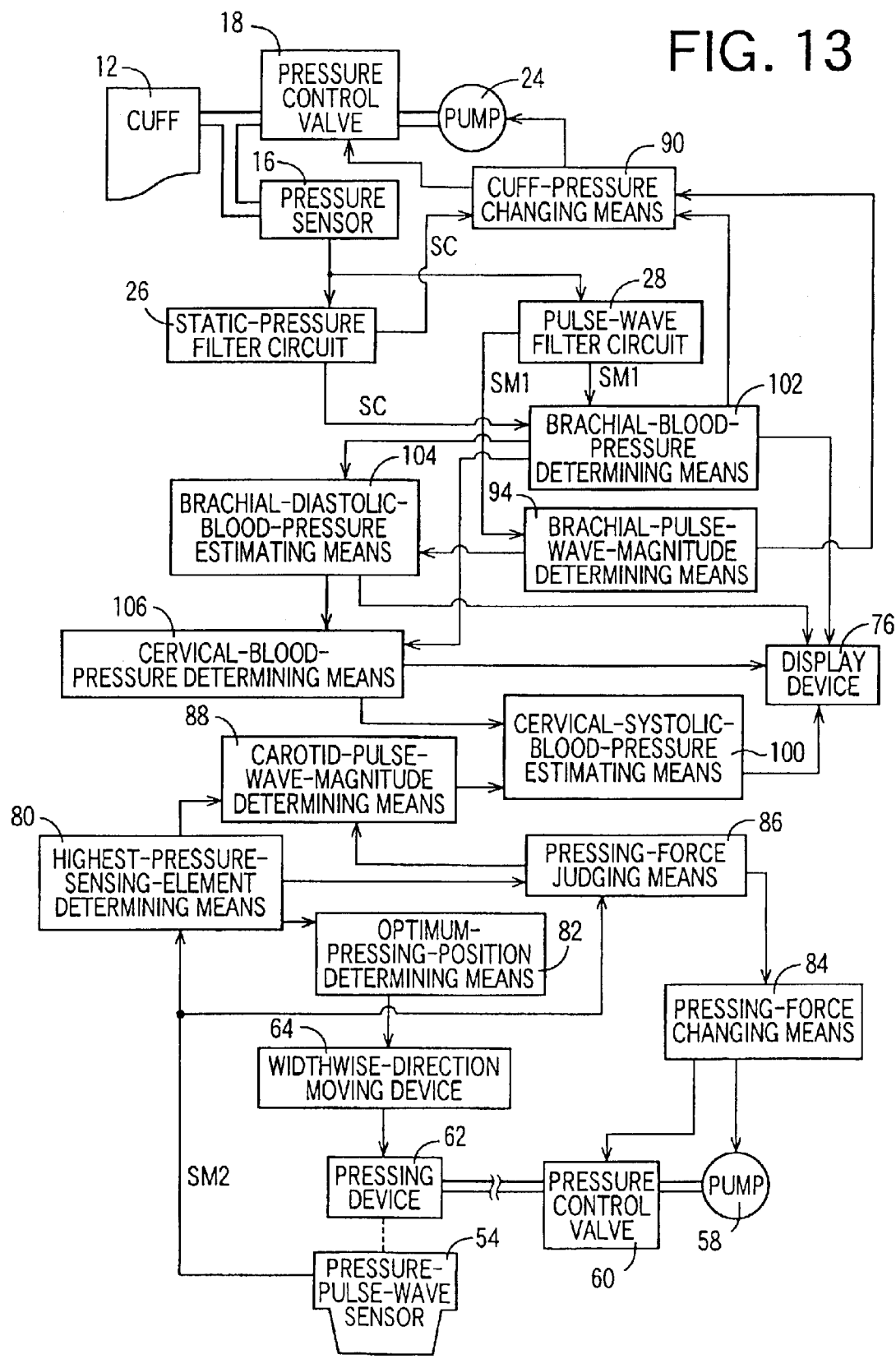
FIG. 13 is a block diagram for explaining essential control functions of an electronic control device of another neck-blood-pressure determining apparatus different from the apparatus shown in FIG. 1.

The cervical-blood-pressure determining apparatus 10 may be so modified as to employ the above-indicated feature. FIG. 13 is a diagrammatic view for explaining essential control functions of an electronic control device 32 as part of the thus modified cervical-blood-pressure determining apparatus. The same reference numerals as used in the embodiment shown in FIGS. 1 through 12 are used to designate the corresponding elements of the embodiment shown in FIG. 13, and the description of those elements is omitted.

In FIG. 13, a brachial-blood-pressure determining device or means 102 determines, based on a cuff-pressure signal SC continuously supplied from a static-pressure filter circuit 26, and a cuff-pulse-wave signal SM1 continuously supplied from a pulse-wave filter circuit 28, each during slow decreasing of a cuff pressure PC under control of a cuff-pressure changing means 90, a systolic blood pressure BBP(SYS) and a mean blood pressure BBP(MEAN) of a brachial portion of a living subject, according to a well-known oscillometric algorithm. According to the oscillometric algorithm, the determining means 102 determines an envelope of respective amplitudes A of respective heartbeat-synchronous pulses of a brachial pulse wave wb, and determines, as the brachial systolic blood pressure BBP(SYS), a value of the cuff pressure PC at the time of detection of a rising point of the envelope and additionally determines, as the brachial mean blood pressure BBP(MEAN), a value of the cuff pressure PC at the time of detection of a peak point of the envelope, i.e., a maximum amplitude of the brachial pulse wave wb.

A brachial-diastolic-blood-pressure estimating device or means 104 as a first-diastolic-blood-pressure estimating means estimates a diastolic blood pressure BBP(DIA) of the brachial portion of the subject, based on the brachial systolic and mean blood pressure values BBP(SYS), BBP(MEAN) determined by the brachial-blood-pressure determining means 102, and a minimum magnitude d, an area-gravity-center magnitude e, and a maximum magnitude f of the brachial pulse wave wb determined by a brachial-pulse-wave-magnitude determining means 94. As described previously, since the minimum magnitude d of the brachial pulse wave wb corresponds to the brachial diastolic blood pressure BBP(DIA), the area-gravity-center magnitude e of the brachial pulse wave wb corresponds to the brachial mean blood pressure BBP(MEAN), and the maximum magnitude f of the brachial pulse wave wb corresponds to the brachial systolic blood pressure BBP(SYS), the estimating means 104 calculates the brachial diastolic blood pressure BBP(DIA) by replacing the above-indicated Expression 2 with the brachial systolic and mean blood pressure values BBP(SYS), BBP(MEAN) determined by the brachial-blood-pressure determining means 102 and the area-gravity-center and maximum magnitudes e, f of the brachial pulse wave wb determined by the brachial-pulse-wave-magnitude determining means 94.

A cervical-blood-pressure determining device or means 106 determines the brachial mean blood pressure BBP(MEAN) as determined by the brachial-blood-pressure determining means 102, as a mean blood pressure CBP(MEAN) of the cervical portion of the subject, and additionally determines the brachial diastolic blood pressure BBP(DIA) as estimated by the brachial-diastolic-blood-pressure estimating means 104, as a diastolic blood pressure CBP(DIA) of the cervical portion of the subject. Moreover, the determining means 106 operates a display device 76 to display the thus determined cervical diastolic and mean blood pressure CBP(DIA), CBP(MEAN).

The present invention may be embodied with other various changes without departing from the spirit of the invention.

What is claimed is:

1. A blood-pressure estimating apparatus, comprising:

a first-pulse-wave detecting device which detects a first pulse wave from a first portion of a living subject;

a blood-pressure measuring device which includes an inflatable cuff adapted to be worn on the first portion of the subject and measures, with the cuff, a diastolic blood pressure and a systolic blood pressure of the first portion of the subject;

a mean-blood-pressure estimating means for converting, based on a minimum magnitude and a maximum magnitude of the first pulse wave detected by the first-pulse-wave detecting device and the diastolic blood pressure and the systolic blood pressure measured by the blood-pressure measuring device, a magnitude of a gravity center of an area defined by the first pulse wave into an estimated mean blood pressure of the first portion of the subject;

a second-pulse-wave detecting device which detects a second pulse wave from a second portion of the subject; and a systolic-blood-pressure estimating means for converting, based on the diastolic blood pressure measured by the blood-pressure measuring device and the mean blood pressure estimated by the mean-blood-pressure estimating means, a maximum magnitude of the second pulse wave detected by the second-pulse-wave detecting device into an estimated systolic blood pressure of the second portion of the subject.

2. A blood-pressure estimating apparatus according to claim 1, wherein the first portion and the second portion of the subject are a brachial portion and a cervical portion of the subject, respectively.

3. An apparatus according to claim 1, wherein the second-pulse-wave detecting device comprises a pressure-pulse-wave sensor which is adapted to be pressed against an artery of the second portion of the subject and detects, as the second pulse wave, a pressure pulse wave produced from the artery.

4. An apparatus according to claim 1, further comprising a display device which displays at least one of the mean blood pressure estimated by the mean-blood-pressure estimating means and the systolic blood pressure estimated by the systolic-blood-pressure estimating means.

5. A blood-pressure estimating apparatus, comprising:

a first-pulse-wave detecting device which detects a first pulse wave from a first portion of a living subject;

a blood-pressure measuring device which includes an inflatable cuff adapted to be worn on the first portion of the subject and measures, with the cuff, a mean blood pressure and a systolic blood pressure of the first portion of the subject;

a diastolic-blood-pressure estimating means for converting, based on an area-gravity-center magnitude and a maximum magnitude of the first pulse wave detected by the first-pulse-wave detecting device and the mean blood pressure and the systolic blood pressure measured by the blood-pressure measuring device, a minimum magnitude of the first pulse wave into an estimated diastolic blood pressure of the first portion of the subject;

a second-pulse-wave detecting device which detects a second pulse wave from a second portion of the subject; and a systolic-blood-pressure estimating means for converting, based on the mean blood pressure measured by the blood-pressure measuring device and the diastolic blood pressure estimated by the diastolic-blood-pressure estimating means, a maximum magnitude of the second pulse wave detected by the second-pulse-wave detecting device into an estimated systolic blood pressure of the second portion of the subject.

6. A blood-pressure estimating apparatus according to claim 5, wherein the first portion and the second portion of the subject are a brachial portion and a cervical portion of the subject, respectively.

7. An apparatus according to claim 5, wherein the second-pulse-wave detecting device comprises a pressure-pulse-wave sensor which is adapted to be pressed against an artery of the second portion of the subject and detects, as the second pulse wave, a pressure pulse wave produced from the artery.

8. An apparatus according to claim 5, further comprising a display device which displays at least one of the diastolic blood pressure estimated by the diastolic-blood-pressure estimating means and the systolic blood pressure estimated by the systolic-blood-pressure estimating means.

* * * * *